(12) United States Patent
Ueda

(10) Patent No.: US 7,150,987 B2
(45) Date of Patent: Dec. 19, 2006

(54) ORGANIC WASTE PROCESSING METHOD AND DEVICE THEREFOR

(75) Inventor: Yasuichi Ueda, Okinawa (JP)

(73) Assignee: Japan Life Center, Inc., Okinawa (JP)

( * ) Notice: Subject to any disclaimer, the term of this patent is extended or adjusted under 35 U.S.C. 154(b) by 371 days.

(21) Appl. No.: 10/240,375

(22) PCT Filed: Feb. 14, 2001

(86) PCT No.: PCT/JP01/01047

§ 371 (c)(1),
(2), (4) Date: Sep. 27, 2002

(87) PCT Pub. No.: WO01/72441

PCT Pub. Date: Apr. 10, 2001

(65) Prior Publication Data

US 2003/0111413 A1    Jun. 19, 2003

(30) Foreign Application Priority Data

Mar. 29, 2000    (JP)    ............................. 2000-092272

(51) Int. Cl.
C05F 17/02    (2006.01)
(52) U.S. Cl. ................ 435/262; 435/290.2; 435/290.4; 435/294.1; 71/9
(58) Field of Classification Search .. 435/290.1–290.4, 435/294.1, 291.4, 262; 71/8–10; 366/196, 366/263, 265; 422/269; 210/255
See application file for complete search history.

(56) References Cited

U.S. PATENT DOCUMENTS 4,252,901 A * 2/1981 Fischer et al. .............. 435/167

5,810,903 A * 9/1998 Branconnier et al. ............ 71/9

FOREIGN PATENT DOCUMENTS

| EP | 1264644 A1 | * | 12/2002 |
| JP | 06312168 A | * | 11/1994 |
| JP | 9-255463 | | 9/1997 |
| JP | 11151472 A | * | 6/1999 |
| JP | 11199356 A | * | 7/1999 |

OTHER PUBLICATIONS

English language machine translation of JP 09-255463 (Jul. 25, 2005).*
English language machine translation of JP 11-199356 (Jul. 25, 2005).*

* cited by examiner

Primary Examiner—William H. Beisner
(74) Attorney, Agent, or Firm—Leighton K. Chong; Godbye Griffiths Reiss & Chong

(57) ABSTRACT

An organic waste processing method and device makes a mass disposal and 24 hours continuous processing possible, and can largely cut down facility and processing costs. It uses a number of roughly cut-end inverted cone shaped processing tanks 3, 3A, 3B, and 3C aligned serially, a motor 17 installed on the bottom of each processing tank, a rotating shaft 19 that rotates by motor 17 drive set up passing through the top and bottom parts inside each processing tank, and stirring blades 21, attached on rotating shaft 19, that mix aerobic microorganism 1 and organic waste 2 to put in more than capacity amount of organic waste 2 into the upstream processing tank 3, have a part of organic waste 2 transport from outlet 14 at upper peripheral wall of processing tank 3 to inlet 9 at the top of processing tank 3A placed adjacently and downstream, by centrifugal force of stirring blades 21. By repeating this process according to the number of processing tanks, a large amount of organic waste 2 is continuously aerobic fermented and turned into compost.

5 Claims, 5 Drawing Sheets

(a)

(b)

(c)

ORGANIC WASTE PROCESSING METHOD AND DEVICE THEREFOR

This U.S. patent application claims the priority of PCT International Application No. PCT/JP01/01047, filed on Feb. 14, 2001, based on the priority of Japanese Patent Application No. 2000-92272 filed on Mar. 29, 2000.

FIELD OF THE INVENTION

The present invention relates to an organic waste processing method and device which efficiently turn organic waste such as scraps of food and raw garbage into compost in a relatively short time by fermentation disposal.

DESCRIPTION OF PRIOR ART

For disposal of organic waste such as leftovers and raw garbage, there are variety of methods such as method by electrically powered raw garbage disposal device and method by directly applying underground. As one of the methods, there is a fermentation disposing method that can turn organic waste into safe compost.

However, simply operating fermentation disposing method could bring problems such as decay of organic waste and infestation of maggots. Especially for an operation of fermentation disposing method, it is necessary to be knowledgeable about characteristics of aerobic microorganism and raw garbage compost (for example, the principle of microorganism that elevates temperature by giving off fermentation heat when environmental status is developed; and the fact that when fermentation disposal is operated in a tank, the fermentation disposal proceeds evenly between top part, middle part, and bottom part), and being skilled in the mechanical technology alone is insufficient. Therefore, for instance, ignoring the fermentation temperature of aerobic microorganism and simply applying heat by a heating device could cause delay in disposing time and rise in running cost, and make industrialization of production line difficult.

The present invention is in consideration of the above. This invention avoids decay of organic waste and infestation of maggots, and prevents delay in disposing time and curbs the rise of running cost, and moreover, this invention aims to provide organic waste processing method and device which could be easily industrialized.

The present invention also aims to provide organic waste processing method and device which is capable of large amount processing, 24 hours continuous processing, and which could significantly reduce facility and processing cost, by providing massive and continuous processing system that is not restricted to fermenter capacity.

DISCLOSURE OF THE INVENTION

To achieve the above-mentioned task, an organic waste processing method aerobic ferments organic waste and turns into compost, by using a number of roughly cut-end inverted cone shaped processing tanks that have organic waste with aerobic microorganism implanted aligned, motor to be set up on either top or bottom of each processing tank, rotating shaft supported by either top or bottom of each processing tank at least that rotate by motor drive, and by stirring blades that are installed to the rotating shaft and mix aerobic microorganism and organic waste. The invention is characterized in that it puts in organic waste more than its intake capacity into the upstream processing tank, transports a part of organic waste from the outlet at the upper part of the peripheral wall of the upstream processing tank to the downstream processing tank placed adjacent by centrifugal force of stirring blades, and repeats depending on the a number of processing tanks.

The invention uses a number of processing tanks that have organic waste with aerobic microorganism implanted and that aerobic ferment organic waste and turn into compost, and is characterized in that a number of processing tanks are aligned and the outlet at the upper part of the peripheral wall of the upstream processing tank and the inlet on the top of downstream processing tank placed adjacent are connected, each processing tank is formed in the shape of roughly cut-end inverted cone and a motor is set up on either top or bottom of each processing tank, rotating shaft is supported by either top or bottom of each processing tank at least that rotate by motor drive, and stirring blades are installed to the rotating shaft that mix aerobic microorganism and organic waste.

In addition, it is desirable to place a number of thermo sensors on the inner peripheral wall of each processing tank and to align these thermo sensors vertically at specified intervals.

Moreover, it is desirable to install an insulating material to the peripheral wall of each processing tank and substantially seal organic waste in these processing tanks.

Furthermore, it is possible to install cutter blades that grind and mix aerobic microorganism and organic waste to rotating shaft and/or stirring blades.

The aerobic microorganisms could be various aerobe, filamentous bacteria, or actinomycetes. Organic wastes include leftovers, fish head, pig bone, livestock dropping, sawdust, cardboard, raw garbage, and any other organic waste. Organic waste could be persistent or not. A number of processing tanks could be three, five, or six as long as there are more than two. Also, stirring blades are mainly plural in number, but it does not especially specify the number. Also, stirring blades are mainly plural in number, but it does not especially specify the number.

According to the invention, large amount of organic waste is continuously put in and expelled in a number of connected processing tanks instead of a single processing tank. Compared to the composting disposal using one processing tank, the fermentation efficiency could be raised. In addition, fermentation disposal could be done unlimited to the capacity of processing tank because large amount of organic waste is continuously transported in a number of processing tanks from upstream to downstream. Moreover, continuous fermentation disposing eliminates the need to put in and expel organic waste, speeds up the increase of fermentation temperature of organic waste, and makes it possible to shorten the process when processing the same amount.

According to the invention, a number of thermo sensors are placed on the inner peripheral wall of each processing tank and are aligned vertically at specified intervals, therefore, it is possible to grasp the temperature distribution of top, center, and bottom, or top and bottom of organic waste and control the motor rotation.

According to the invention, a insulating material is installed to the peripheral wall of each processing tank and organic waste is substantially sealed in these, therefore, it is possible to avoid the heat caused by organic waste decomposition from escaping outside. Hence, it can increase the fermentation temperature of organic waste approximate linearly under small heat loss decomposition condition. Moreover, fermentation is done under substantially sealed condition, in other words, a pressure retaining condition, therefore, it is possible to increase fermentation temperature in a short time (under a certain condition, increase higher than 100 degrees Celsius in less than 90 minutes).

Furthermore, according to the invention, singular or plural number of cutter blades that grind and mix aerobic microorganism and organic waste are installed directly or indirectly to rotating shaft and/or stirring blades, therefore, it is possible to accelerate organic waste fermentation with relatively small rotational resistance.

BRIEF EXPLANATION OF THE DRAWINGS

FIG. 3(a) is an explanatory diagram showing slanted puddle type stirring blades; FIG. 3(b) is an explanatory diagram showing turbine type stirring blades; and FIG. 3(c) is an explanatory diagram showing anchor type stirring blades.

DESCRIPTION OF THE PREFERRED EMBODIMENTS

Figure 1:
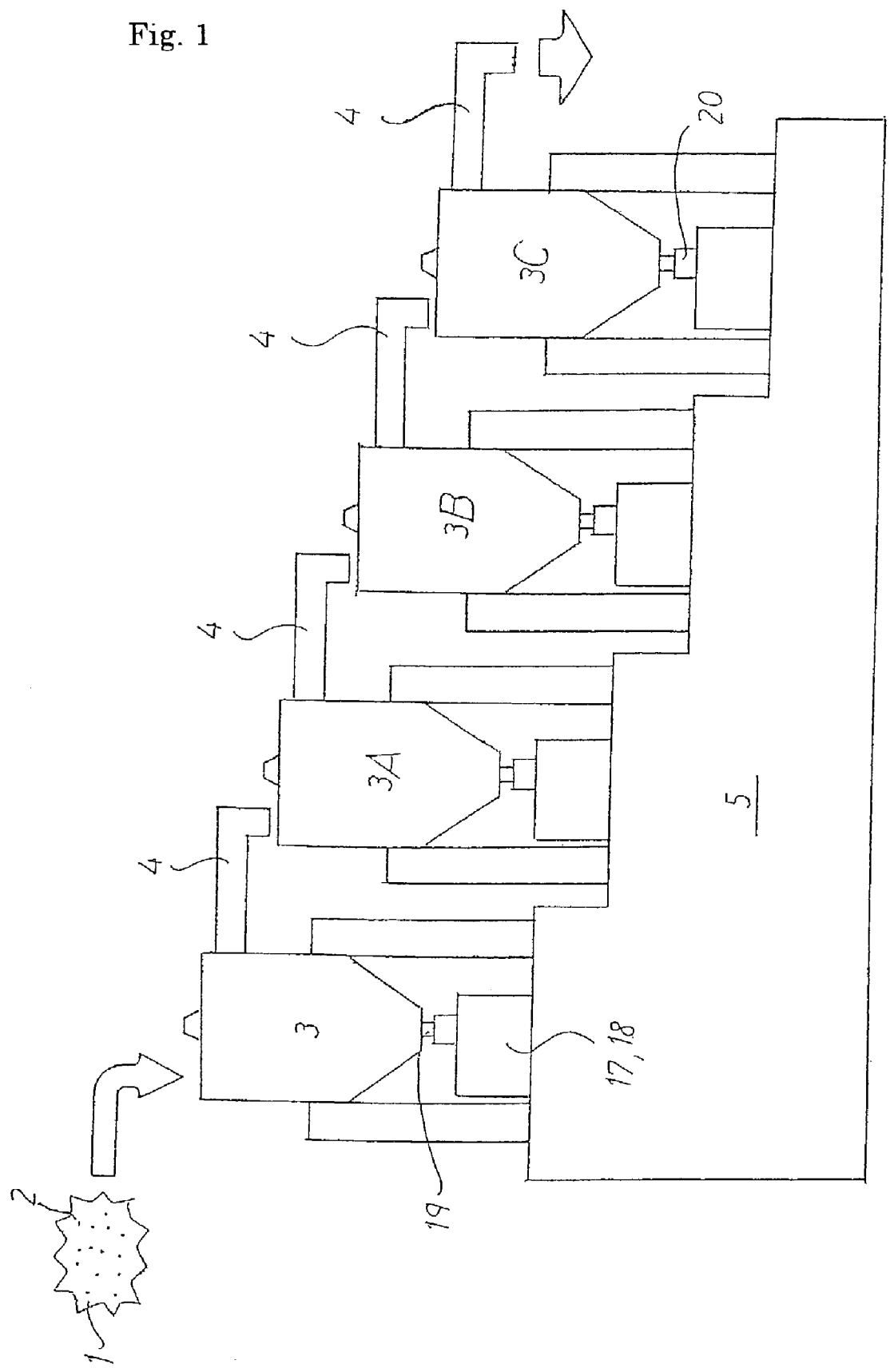
FIG. 1 is an explanatory diagram showing an embodiment of an organic waste processing method and device according to the present invention.

A detailed explanation of the best mode for carrying out the present invention is made referring to the drawings. An organic waste processing method and device in the present embodiment, as shown in FIGS. 1 and 2, processing tanks 3, 3A, and 3B that substantially seal organic waste 2 with aerobic microorganism implanted beforehand are aligned from upstream to downstream, outlet 14 on the upper part of each medium-sized processing tank 3, 3A, 3B, and 3C and inlet 9 on the top part of processing tanks 3A, 3B, and 3C placed downstream and adjacent are connected by passage 4, motor 17 is installed on the bottom part of each processing tank 3, 3A, 3B, and 3C, and at the same time, rotating shaft 19 that rotates by motor 17 drive is set up passing through the top and bottom parts inside each processing tank 3, 3A, 3B, and 3C, a number of stirring blades 21 that mix aerobic microorganism 1 and organic waste 2 are installed on rotating shaft 19, and a large amount of organic waste 2 is continuously aerobic fermented and turned into compost.

Aerobic microorganism 1 is comprised of various aerobes that require oxygen, filamentous bacteria, and actinomycetes. This aerobic microorganism 1 is dominant state in nature because it is characterized in that it has respiration that is biologically highest in energy efficiency, and it has proliferation rate that is faster compared to anaerobes.

A number of processing tanks (in the present embodiment, four) 3, 3A, 3B, and 3C are, as shown in FIG. 1, set up on the stand 5 in a straight single horizontal row. From this setting, a number of processing tanks 3, 3A, 3B, and 3C have the top processing tank 3 at the highest position, processing tanks 3A and 3B at positions gradually lowered than the one before, and the lowest processing tank 3C at the lowest position.

Figure 2:
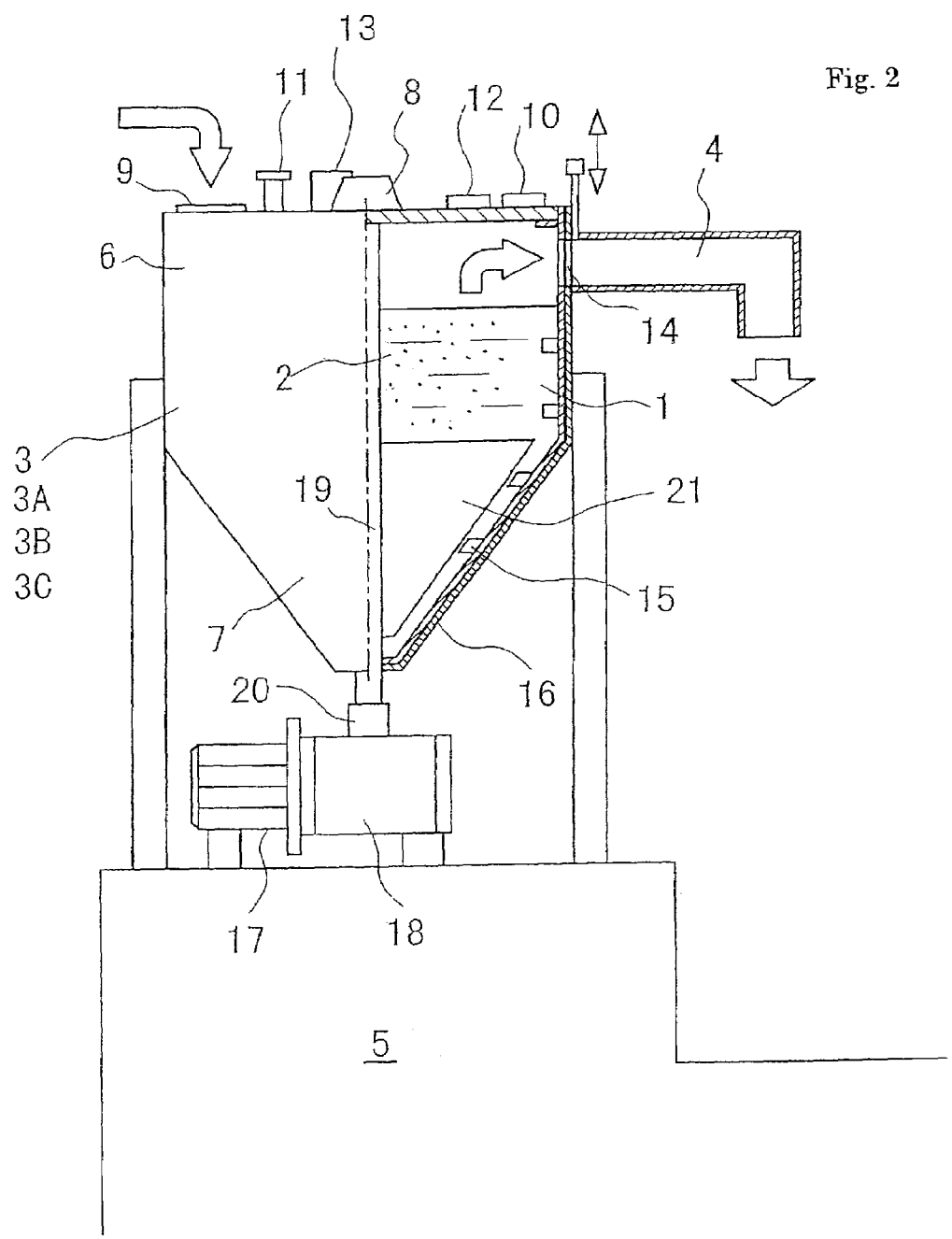
FIG. 2 is a sectional explanatory diagram showing an embodiment of an organic waste processing method and device according to the present invention.

Each processing tank 3, 3A, 3B, and 3C is, as shown in FIG. 2, formed by such materials as aluminum, aluminum alloy, and steel in the shape of hollow and roughly cut-end inverted cone with the height of 100 cm or less. Each processing tank 3, 3A, 3B, and 3C is equipped with cylindrical large diameter part 6 placed in the upper section, roughly cut-end inverted cone shaped small diameter part 7 is placed integrally and continuously in the lower section, and is functioned so that more organic waste 2 can be stored at the large diameter part 6 than organic waste 2 to be blended at the small diameter part 7. To explain this point, organic waste 2 such as raw garbage is characterized in that it reduces volume by grinding and mixing, and reduces more when the fermentation disposal progresses. Therefore, each processing tank 3, 3A, 3B, and 3C has organic waste 2 in the small diameter part 7 and organic waste 2 in the large diameter part 6 are mixed in a swirl when stirred and reduced in volume, and at the same time, large diameter part 6 is a space to guarantee contact with oxygen.

Each processing tank 3, 3A, 3B, and 3C comprises axis supporting part 8 for rotating shaft 19 at the flat top center part, axis supporting part 8 having a bearing built in, on the flat top part from the center to outward, an inlet 9 for organic waste 2, window 10 for observing inside, an installing nozzle 11 for the thermometers, a lighting nozzle not shown, a controlling panel 12, and an expel duct 13 to expel carbon dioxide, steam and so on that are inside processing tanks 3, 3A, 3B, and 3C. The controlling panel 12 controls motor 17 and so on. At the upper part of peripheral wall, each processing tank 3, 3A, 3B, and 3C, an outlet 14 to adjust degrees of the lid opening is set up long sideways, and the compost is expelled downstream from this outlet 14 to processing tank at the lower position. For example, when planning to put in 60 kg of organic waste 2, this outlet 14 may be formed in the range of 20 cm from the top part of peripheral wall on each processing tank 3, 3A, 3B, and 3C.

At the inner walls of each processing tank 3, 3A, 3B, and 3C, a number of thermo sensors 15 such as thermistor are installed vertically at specified intervals, and these thermo sensors 15 functions to output detection signals to the controlling panel 12. Moreover, at the outer walls of each processing tank 3, 3A, 3B, and 3C, an insulating material 16 made of asbestos and glass wool is integrally applied around, and this insulating material 16 effectively avoids heat from transporting out from processing tanks 3, 3A, 3B, and 3C.

The motor 17 is made of cheap general-purpose AC motor or DC motor, loaded on the stand 5, and able to mix organic waste 2 well enough by, for example, rotating at a rate of about 110 revolutions per minute. This motor 17 is connected with decelerator 18 and an output axis of this decelerator 18 is placed at the bottom center of processing tanks 3, 3A, 3B, and 3C. Furthermore, rotating shaft 19 has its upper part supported by the bearing of axis supporting part 8, its lower part supported by the bearings of processing tanks 3, 3A, 3B, and 3C, and at the same time connected to output axis of the decelerator 18 through joint 20 and the sealing device. To this rotating shaft 19, a number of stirring blades 21 pointing in the diameter direction of processing tanks 3, 3A, 3B, and 3C are set up radiately through a connector, and each of this metal stirring blade 21 mixes aerobic microorganism 1 and organic waste 2.

In the above-mentioned structure, to dispose organic waste 2 such as leftovers and raw garbage, first of all empty all processing tanks 3, 3A, 3B, and 3C, implant aerobic microorganism 1 to the organic waste 2 such as raw garbage, and put in a large amount of organic waste 2 into the inlet 9 of the most upstream processing tank 3 continuously.

Regarding the amount of organic waste 2 to put in, it is desirable to put in as much amount as possible over its capacity because larger amount accelerates fermentation disposal progress more. If fish heads and pig bones are in the organic waste 2, it is recommended to grind them to the moderate size by a grinder (for example, jaw crusher, corn crusher, or hammer mill) beforehand.

Moreover, if the percentage of moisture content of organic waste 2 is over 66%, drain or dry to adjust the percentage of moisture content of organic waste 2 to 45~65% or less (moisture standard) so that aerobic microorganism 1 can be active and an offensive odor can be avoided. Also, implantation of aerobic microorganism 1 can be done before or after such process. At the time of implanting aerobic microorganism 1, it is possible to ensure the balance of carbon and nitrogen by mixing carbon source such as dead leaves and dead grasses to control dispersion of nitrogen.

After putting more than tank's capacity of organic waste 2 into the most upstream processing tank 3 with the same pressure kept, drive the motor 17 to continuously rotate the rotating shaft 19 at the rate of about 110 revolutions per minute, grind and mix organic waste 2 and aerobic microorganism 1 well with stirring blades 21 to put properties of organic waste 2 in order, put conditions of decomposition by aerobic microorganism 1 in order to make organic waste 2 more smaller, and fermentation dispose organic waste 2 at the specified temperature. Incidentally, ignoring the fermentation temperature of aerobic microorganism and simply applying heat by a heating device could cause delay in disposing time and rise in running cost, and make industrialization of production line difficult. In the present invention, however, organic waste 2 is self heat generated by a simple structure and the fermentation temperature is controlled. At this fermentation disposing, namely, because organic waste 2 is self heat generated by a simple structure, not heated up outside by some heating device, transitions such as increase, constancy, and decrease in its fermentation temperature are observed by a number of thermo sensors 15 ceaselessly. To increasing fermentation temperature of organic waste 2, and to make the processing time short, rotational rate of the motor 17 is raised up, in other words, rotational rate of rotating shaft 19 is increased manually or by automatic control. Conversely, to decrease the fermentation temperature of organic waste 2 for the economic/cost reasons, lower rotational rate of the motor 17, in other words, rotational rate of rotating shaft 19 is dropped manually or by automatic control.

Furthermore, when more than tank's capacity of organic waste 2 is put into the most upstream processing tank 3 continuously, overflowed organic waste 2 is expelled, by potential energy and horizontal centrifugal force of stirring blades 21, from the outlet 14 of the processing tank 3 to the inlet 9 of the adjacent and downstream processing tank 3A. This is repeated depending on the number of processing tanks 3, 3A, 3B, and 3C, and the organic waste 2 continuously expelled to the most downstream processing tank 3C. As organic waste 2 is transported continuously through processing tanks 3, 3A, 3B, and 3C, the amount of microorganism is increased and the fermentation temperature rises gradually (for example, 20, 40, 65, and 90 degrees Celsius) and the first fermentation is completed.

Next, organic waste 2 is aerobic fermented and turn into compost, and when compost is obtained, compost shown by the arrow is expelled from each processing tank 3, 3A, 3B, and 3C. After that, by putting compost into fields, fertilizer components are provided to crops and microorganisms in the soil are activated. Repeat the above-mentioned procedures as much as necessary.

According to the above-mentioned structure, a large amount of organic waste 2 can be continuously put in and continuously expelled for 24 hours and on, fermentation efficiency can be largely improved compared to each composting disposal. Also, a number of processing tanks 3, 3A, 3B, and 3C continuously transport large amount of organic waste 2 from upstream to downstream, therefore fermentation disposal can be operated without a limit of capacity in processing tanks. Moreover, when one of the processing tanks failed, it can evade that processing tank and continuously transport a large amount of organic waste 2, and it can avoid stopping the system as a whole. Furthermore, since it is a continuous fermentation disposal, putting in and expelling organic waste 2 each time is not necessary, fermentation temperature of organic waste 2 is faster, and can count on shortening the process. What is more, in the second and the steps, remaining heat energy can be used and temperature fall by putting organic waste is truly small.

Organic waste 2 is self heat generated by a simple structure, not heated up outside by some heating device, and its fermentation temperature is controlled by the motor 17, therefore, it is possible to largely avoid delay in the processing time and rise in the running cost. Also, since it is a simple structure, it can expect the production line to be industrialized. Moreover, it is possible to easily obtain compost with less offensive odor density because organic waste 2 is self heat generated at high temperature. Therefore, under such high temperature condition obtained by organic waste 2 self generating heat, unlike raising temperature by heating from outside, solid and liquid of organic waste 2 are reduced well balanced and high temperature is reached without losing decomposition conditions of microorganisms. As a result, volatile component among easily decomposed component in the organic waste 2, and compost with low offensive odor density is easily obtained after the disposal. From all the above, improvement of the soil using the compost, therefore create productive agriculture, avoid agricultural chemical contamination, improve agricultural self-sufficiency, and accelerate assimilation of global warming gas from plants.

Figure 3:
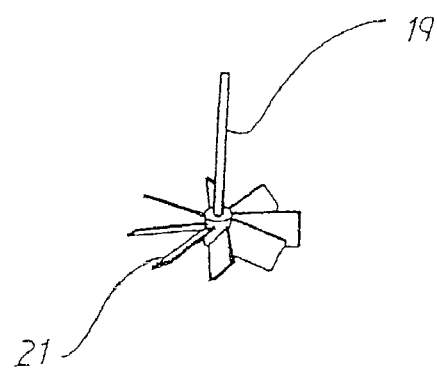
FIG. 3 is an explanatory diagram showing stirring blades in other embodiments of an organic waste processing method and device according to the present invention.
Figure 3:
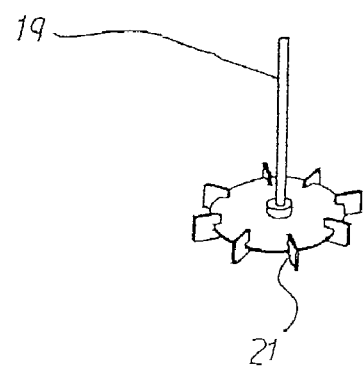
Figure 3:
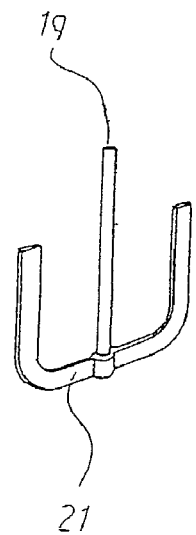
Figure 4:
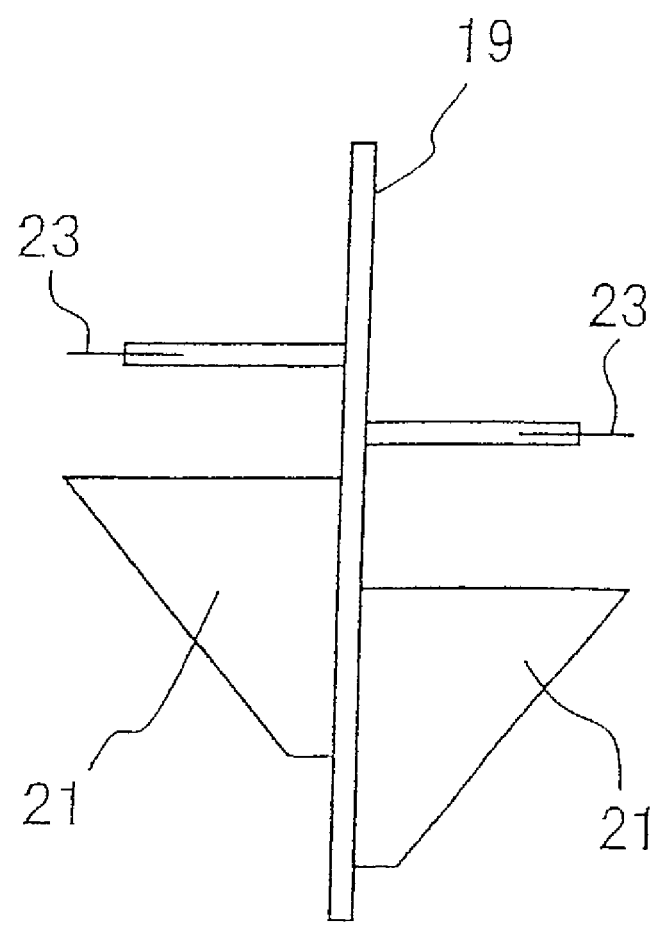
FIG. 4 is an explanatory diagram showing cutter blades in other embodiments of an organic waste processing method and device according to the present invention.

In the above-mentioned embodiment, a large amount of organic waste 2 was continuously put into the inlet 9 of the most upstream processing tank 3, however it is not limited to that and a large amount of organic waste 2 can be put into inlet 9 of each processing tank 3, 3A, 3B, and 3C. Moreover, processing tanks 3, 3A, 3B, and 3C can be set up on the stand 5 in 20~50 degrees vertical inclination to lighten the burden imposed on stirring blades 21. Motor 17 and decelerator 18 can be positioned on the top center of disposition tanks 3, 3A, 3B, and 3C. As shown in FIGS. 3 (a), (b), and (c), number and shape of stirring blades 21 can be changed suitably. As shown in FIG. 4, one or a number of cutter blades 22 that grind and mix aerobic microorganism 1 and organic waste 2 can be installed on rotating shaft 19 and/or stirring blades 21 and cut down or omit the grinding device.

An explanation of the embodiment of organic waste processing method and device according to the present invention will be made in the following.

As shown in FIG. 1, four processing tanks 3, 3A, 3B, and 3C are aligned serially from upstream to downstream having outlet 14 on the upper peripheral wall of each processing tank 3, 3A, and 3B and inlet 9 on the top part of processing tanks 3A, 3B, and 3C placed adjacently and the downstream from the former of each tank are connected by passage 4, have motor 17 installed on the bottom part of each processing tank 3, 3A, 3B, and 3C, and at the same time, rotating shaft 19 that rotates by motor 17 drive is set up passing through the top and bottom parts inside each processing tank 3, 3A, 3B, and 3C, and a number of stirring blades 21 that mix aerobic microorganism 1 and organic waste 2 are attached on rotating shaft 19. By using this organic waste processing device, a large amount of organic waste 2 is continuously aerobic fermented and turned into soil, and change of fermentation temperature of organic waste 2 is measured.

Figure 5:
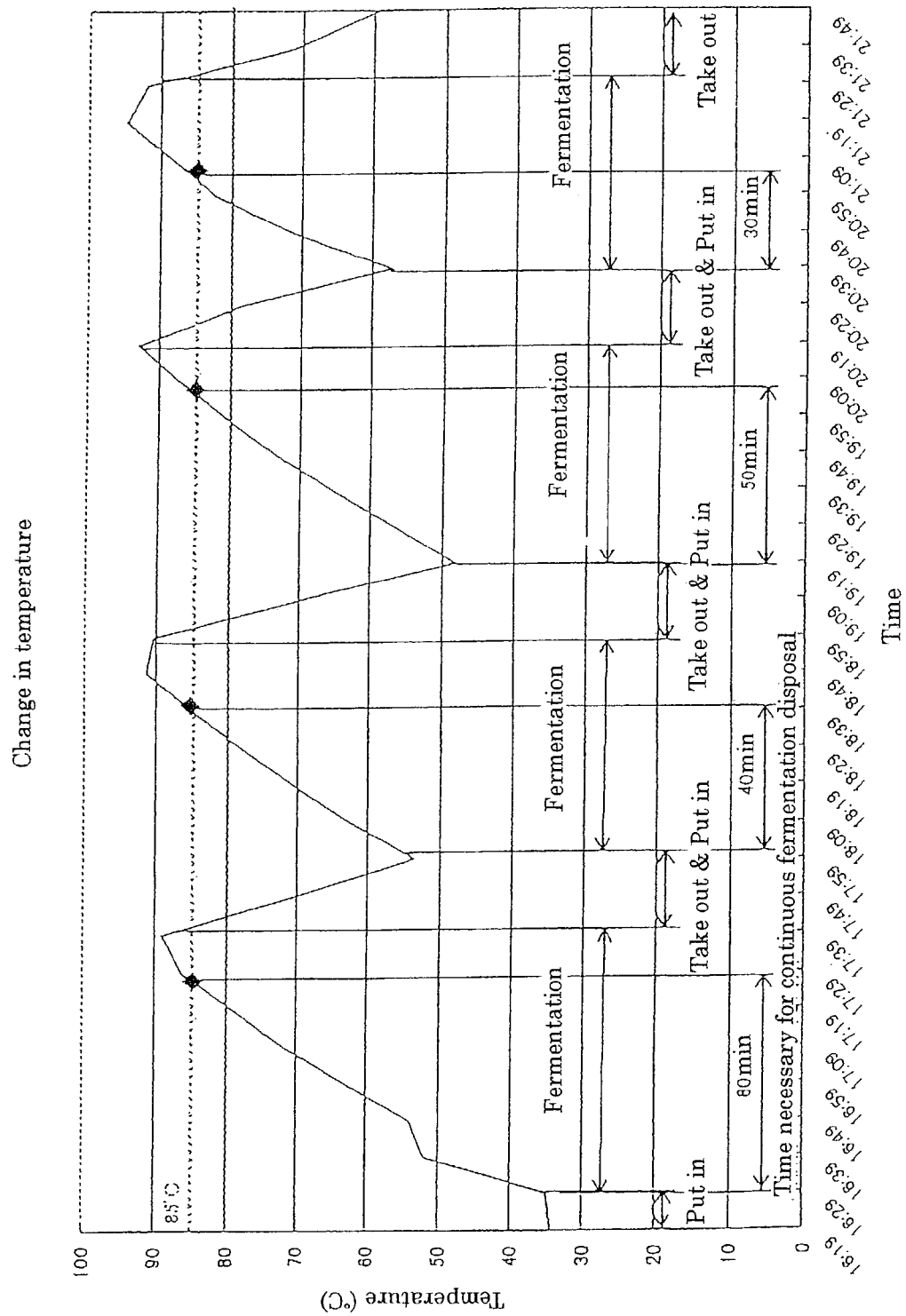
FIG. 5 is a graph of an embodiment of an organic waste processing by using single processing tank.

By using single processing tank, a large amount of organic waste is continuously aerobic fermented and turned into soil, and change of fermentation temperature of organic waste is shown in FIG. 5. In the disposal, fermentation temperature was set at 80 degrees Celsius and disposal completion time was set up at 5 minutes and over.

Result

Reduction of Average Processing Time

It took 4 hours and 30 minutes to process organic waste by using four processing tanks to the present invention, while it took 5 hours and 30 minutes by comparison with single processing tank. The average time was about 67 minutes.

Increase of the Lowest Temperature

In putting in organic waste 2, the fall of the disposing temperature in the second disposal or more was less than that in the first disposal. This is because the quantity of heat in the processing device was high.

Increase of the Highest Temperature

In a generally use of the processing device, the temperature raised well and did not take too long to reach 90 degrees Celsius. Bad molds are usually sterilized by heat of 90 degrees Celsius and over.

Consideration Based on FIG. 5

In the continuous fermentation disposal, compared with single fermentation disposal, it does not need to take out or put in outside the processing device. Therefore the processing time by a number of processing tanks is shortened than that by single processing tank, when processing the same amount the original way. Also, change of fermentation temperature of organic waste by using single processing tank shown in FIG. 5 included the periods between "Take Out and Put in". In the present invention, those processes are not necessary. Furthermore, 85 degrees Celsius and over of fermentation temperature is not necessary to dispose organic waste. So, it was calculated 60+40+50+30=180 minutes in total of four tanks from putting in organic waste to increasing inside temperature of each processing tank up to 85 degrees Celsius, therefore average time per tank was 45 minutes.

INDUSTRIAL APPLICABILITY

The present invention according to claim 1 or 2, has effects such as no decay of organic waste and no infestation of maggots, and no delay in processing time and no rise in running cost. Also, since it is a relatively simple structure, it can expect the production line to be industrialized.

Moreover, it is capable of large amount processing and 24 hours continuous processing, and can largely cut down facility and processing costs.

What is claimed is:

1. An organic waste processing method for fermenting organic waste and turning it into compost, comprising the steps of:

providing a plurality of processing tanks, each processing tank being formed of a conical vessel disposed with its narrow end as a bottom of the vessel and being sealed at its top end with a lid that includes a material inlet, said tank further including an outlet located on an uppermost surface of a peripheral wall of the tank, a drive motor, a rotatable shaft connected to the motor, and stirring blades installed on the shaft, the motor, shaft, and blades being constructed extending in a diametral direction of the tank such that centrifugal force generated by the blades allows a part of the material being processed to be mixed in an upward swirl in the tank and to be discharged out of the tank through the outlet, wherein the inlet of each tank vessel in processing succession is provided at an elevation lower than that of the outlet of the preceding tank vessel, and processing organic waste aerobically with microorganisms mixed therein in processing succession through said plurality of processing tanks.

2. An organic waste processing device comprising:

a plurality of processing tanks, each processing tank being formed of a conical vessel disposed with its narrow end as a bottom of the vessel and being sealed at its top end with a lid that includes a material inlet, said tank further including an outlet located on an uppermost surface of a peripheral wall of the tank, a drive motor, a rotatable shaft connected to the motor, and stirring blades installed on the shaft, the motor, shaft, and blades being constructed extending in a diametral direction of the tank such that centrifugal force generated by the blades allows part of the material being processed to be mixed in an upward swirl in the tank and to be discharged out of the tank through the outlet, wherein the inlet of each tank vessel in processing succession is provided at an elevation lower than that of the outlet of the preceding tank vessel.

3. An organic waste processing device according to claim 2, wherein a number of thermo sensors are placed on an inner part of the peripheral wall of each processing tank aligned vertically at a specified interval.

4. An organic waste processing device according to claim 2, wherein an insulating material is installed on the peripheral wall of each processing tank to substantially seal organic waste being processed in the tank.

5. An organic waste processing device according to claim 2, wherein cutter blades are installed on the rotating shaft to grind and mix aerobic microorganisms and organic waste in each processing tank.

* * * * *